United States Patent [19]

Drake et al.

[11] Patent Number: 4,575,575

[45] Date of Patent: Mar. 11, 1986

[54] CATALYSTS AND PROCESS FOR OLEFIN CONVERSION

[75] Inventors: Charles A. Drake; Robert E. Reusser, both of Bartlesville, Okla.

[73] Assignee: Phillips Petroleum Company, Bartlesville, Okla.

[21] Appl. No.: 596,984

[22] Filed: Apr. 5, 1984

[51] Int. Cl.$^3$ .............................................. C07C 3/62
[52] U.S. Cl. ................................................... 585/646
[58] Field of Search ....................................... 585/646

[56] References Cited

U.S. PATENT DOCUMENTS

| | | | |
|---|---|---|---|
| 3,365,513 | 1/1968 | Heckelsberg | 585/643 |
| 3,579,602 | 5/1971 | Reusser | 585/364 |
| 3,586,731 | 6/1971 | Heckelsberg | 585/643 |
| 3,660,506 | 5/1972 | Banks et al. | 585/374 |
| 3,660,507 | 5/1972 | Reusser | 585/374 |
| 3,786,112 | 1/1974 | Reusser et al. | 585/646 |
| 3,792,106 | 2/1974 | Regier | 585/646 |
| 3,865,751 | 2/1975 | Banks et al. | 585/646 |
| 3,915,897 | 10/1975 | Reusser et al. | 502/241 |

*Primary Examiner*—Curtis R. Davis
*Attorney, Agent, or Firm*—S. E. Reiter

[57] ABSTRACT

A process for disproportionation of olefins is disclosed employing a novel catalyst comprising a silica support treated with an oxide or oxide precursor of tungsten and a Group I oxide or compound convertible to the oxide in admixture with a double bond isomerization catalyst.

11 Claims, No Drawings

CATALYSTS AND PROCESS FOR OLEFIN CONVERSION

BACKGROUND

1. Field of the Invention

This invention relates to catalysts. In accordance with one aspect, this invention relates to catalysts useful for the disproportionation of olefins. In a further aspect, this invention relates to a process for the conversion of olefins. In another aspect, this invention relates to a process for the disproportionation of olefinic hydrocarbons. In yet another aspect, the invention relates to a method for preparing catalyst.

2. Description of the Prior Art

The disproportionation, or metathesis, of olefins is a reaction in which one or more olefinic compounds are transformed into other olefins of different molecular weights. The disproportionation of an olefin with itself to produce an olefin of a higher molecular weight and an olefin of a lower molecular weight can also be referred to as self-disproportionation. For example, propylene can be disproportionated to ethylene and cis-, and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

By the term "disproportionation" or "metathesis" throughout this specification is meant the conversion of the feed olefinic (or unsaturated) hydrocarbon to a mixture of olefinic (or unsaturated) hydrocarbons having different numbers of carbon atoms than the feed hydrocarbons.

Many catalysts have been developed for disproportionation. For example, those comprising inorganic oxides containing a catalytic amount of a metal or metal oxide have been employed widely for continuous, fixed-bed conversion of olefins.

One such catalyst comprises a silica support and an oxide of tungsten. The present invention is based upon the discovery of a way to improve the activity of such a catalyst.

OBJECTS OF THE INVENTION

An object of this invention is a catalyst and process which give improved reactant selectivity and product yield upon the conversion of olefins.

Another object of the invention is a catalyst and process which give improved reactant selectivity and product yield upon the disproportionation of olefins.

These and other objects of our invention will become apparent from the disclosure and claims herein provided.

SUMMARY OF THE INVENTION

In accordance with the present invention, a composition is provided comprising:
(a) a first catalyst component comprising:
 (i) a silica support,
 (ii) an oxide of tungsten or a precursor of an oxide of tungsten, and
 (iii) a Group I oxide or compound convertible to the oxide; and (b) a second catalyst component comprising a double bond isomerization catalyst in intimate admixture with the first catalyst component.

In accordance with another embodiment of the invention a process is provided for the disproportionation of olefinic hydrocarbons by contacting the same with a disproportionation catalyst as hereinbefore described.

In accordance with yet another embodiment of the invention a method is provided for the preparation of catalyst compositions as hereinbefore described.

DESCRIPTION OF THE PREFERRED EMBODIMENT

Catalyst

The silica supports employed to prepare the first catalyst component employed in the practice of the invention usually contain a major proportion of silica. Preferred silica supports contain a substantial proportion of silica, e.g. at least 90 percent by weight of silica, preferably at least 99 percent by weight of silica, although still larger proportions of silica can be used. Especially preferred silica supports are high purity silica supports, i.e., have very low levels of sodium (measured as $Na_2O$) and aluminum (measured as $Al_2O_3$). Thus, especially preferred silica supports are those with sodium and aluminum levels each of about 0.2 weight percent (wt. %) and lower. Generally, the silica support has a surface area of at least 10 square meters per gram ($m^2/g$). Preferably, the surface area is at least 50 $m^2/g$ and most preferably, support employed will be a high surface area silica, i.e., support will have a surface area in excess of about 100 $m^2/g$. Another important consideration is the size of the support particles. Generally, greater catalyst activity, i.e., feed conversion, results when smaller catalyst particles such as for example about 10 mm or less are employed.

The oxide of tungsten used to treat the silica support can be an aqueous solution or suspension of tungsten oxide or a tungsten oxide precursor, which is subsequently converted to an oxide of tungsten by calcination. Suitable tungsten oxide or oxide precursors are compounds which are convertible to the oxide form under calcination conditions, such as, for example, the halides, oxides, sulfides, sulfates, nitrates, acetates and the like, and mixtures of any two or more thereof.

Exemplary tungsten compounds include tungsten pentabromide, tungsten dichloride, tungsten tetrachloride, tungsten hexafluoride, tungsten trioxide, tungsten dioxydichloride, tungsten trisulfide, metatungstic acid, orthotungstic acid, ammonium phosphotungstate, ammonium metatungstate and the like and mixtures of any two or more thereof.

The proportion of tungsten oxide or oxide precursor combined with the silica support can vary appreciably, but generally the support will contain at least about 0.1% by weight of the metal, calculated as the oxide and based on the combined weight of tungsten oxide and silica support. Generally, the support will contain an upper limit of about 40% by weight of the metal, calculated as the oxide and based on the combined weight of tungsten oxide and silica support. Amounts of about 0.2 to about 40% by weight of the metal, calculated as the oxide, are preferred, with amounts of about 2 to about 20% by weight of the metal, calculated as the oxide, especially preferred because good catalyst reactivities and product selectivities are obtained.

In addition to applying tungsten oxide or a tungsten oxide precursor to the silica support, in accordance with the invention the support is further treated with a Group I oxide or compound convertible to the oxide form. Suitable compounds include Group I oxides, hydroxides, carbonates, bicarbonates, nitrates, acetates and the like and mixtures of two or more thereof. Preferred are compounds of sodium and potassium for their ready availability and ease of dissolution in commonly employed solvents such as water. Especially preferred for the same reasons are the hydroxides of sodium and potassium, such as for example potassium hydroxide.

The proportion of Group I oxide or compound convertible to the oxide form combined with the silica support can vary appreciably, but generally the support will contain at least about 0.01% by weight of the Group I metal, calculated as the oxide and based on the combined weight of Group I oxide and silica support. Generally amounts of about 0.01 to about 10% by weight of the metal, calculated as the oxide, are useful with amounts of about 0.05 to about 5% by weight of metal, calculated as the oxide, preferred because significant improvements in catalyst performance are observed. Amounts of about 0.1 to about 1% by weight of metal, calculated as the oxide are especially preferred because excellent catalyst performance is achieved with minimal reagent expense.

Other modifying agents which one may wish to incorporate into the silica support-treating solution or to apply to the support either before or after contacting the support with a treating solution containing tungsten oxide or a tungsten oxide precursor and/or Group I oxide or compound convertible to the oxide form may also be employed.

The silica support can be separately treated with a treating solution containing suitable tungsten oxide or tungsten oxide precursors, followed by a treating solution containing suitable Group I oxide or compound convertible to the oxide form. Alternatively the support can separately be treated first with the Group I oxide or compound convertible to the oxide, then with the tungsten oxide or tungsten oxide precursor. Preferably, for ease of catalyst preparation, support can be treated once with a support-treating solution containing suitable amounts of both the tungsten oxide or tungsten oxide precursors and Group I oxide or compound convertible to the oxide.

The silica support and support-treating solution can be contacted in any suitable manner. For example, the silica support and support-treating solution can be mixed in an open vessel, then any excess liquid can be decanted or removed by filtration. Alternatively, the technique of incipient wetness can be employed whereby only enough liquid is employed to thoroughly wet the silica support, with no free residual liquid. Thus, only as much support-treating solution is employed as the silica support can absorb. This can be accomplished, for example, by spraying support-treating solution over a quantity of silica which is being tumbled in a rotating, baffled drum. Such treatment can also be carried out by simply pouring a predetermined quantity of support-treating solution over a quantity of silica support contained in an open vessel. Alternatively, a measured quantity of silica support could be added to a volume of support-treating solution such that all the liquid is imbibed by the added support. Other techniques as are known to those skilled in the art can also be employed. For example, a quantity of silica support may be placed in a tubular reactor, a volume of support-treating solution may be percolated therethrough, followed by further treatment/activation as necessary.

The conditions of silica support/support-treating solution contacting are not critical. Any temperature and any period of contact time is suitable. For convenience, contacting is generally carried out at about room temperature, although higher or lower temperatures can be employed. A time period sufficient to allow the support and reagents to come into intimate contact is all that is necessary. Thus, the silica support and support-treating solution may be brought into contact for as little time as a few seconds to several hours or more, as convenient.

Following contact of the silica support and support-treating solution, any excess liquid can be removed by suitable means, such as, for example, decantation, filtration or the like. The treated support can then be dried to remove absorbed solvent. Any suitable means, as well known by those skilled in the art, may be employed such as, for example, oven drying, passing a vigorous stream of dry (moisture-free) gas over the treated support and the like. For example, the first catalyst component can be dried by heating at an elevated temperature of say about 200° C. or higher by passage of an inert gas such as nitrogen over the first catalyst component. This can be accomplished within the reactor or in other suitable catalyst preparation equipment.

Calcination, when used, is conducted by heating the treated catalyst in the presence of an oxygen-containing gas such as, for example, air, under conditions sufficient to activate the metal oxide or to convert the metal compound present to the activated oxide form. Temperatures in the range of about 350° C. to about 800° C. are generally satisfactory for such calcination. The time for subjecting the first catalyst component to calcination is an amount of time sufficient to activate the first catalyst component. Anywhere from a few minutes to several hours is suitable. Typically, about 15 minutes to about 20 hours of calcination will be sufficient. Preferably, for most efficient use of reaction equipment, the first catalyst component will be subjected to calcination for about 30 minutes to about 6 hours. Typically less time is required at higher temperatures and vice versa. After calcination, the first catalyst component is optionally treated under reducing conditions such as for example with carbon monoxide, hydrogen or a hydrocarbon at a temperature in the range of about 400°–750° C. to enhance the disproportionation activity of the first catalyst component. Such reducing treatment is carried out preferably at about 500°–650° C., because good catalyst activation with reasonably short activation periods of about one to about six hours is achieved. Such optional reducing treatment can suitably be carried out for a period of time ranging from about 1 minute to about 30 hours. If desired the thus-calcined first catalyst component can be further treated with an inert gas such as nitrogen prior to use in a conversion process to remove materials from the catalyst which may have a detrimental effect on subsequent reactions such as the disproportionation reaction.

A wide variety of double bond isomerization catalysts can be used as the second catalyst component in the practice of the invention. Preferred catalysts are those which have little or no polymerization or cracking activity and which are active for double bond isomerization at conditions suitable for obtaining a disproportionated product with the selected disproportionation-catalyst. Suitable catalysts can be selected from among those available in the art, such as the double bond isomerization catalysts listed in H. N. Dunning "Review of Olefin Isomerization," Ind. & Eng. Chem., 45, 551 (March 1953). Some examples of suitable isomerization catalysts include supported phosphoric acid, bauxite, supported alkali metal, alumina-supported cobalt oxide or iron oxide or manganese oxide. Preferred for their ready availability and good results are zinc oxide, magnesium oxide (magnesia), calcium oxide, cerium oxide, thorium oxide, titanium oxide, and the like, and mixtures of any two or more thereof. Excellent results are obtained with magnesium oxide.

Magnesia suitable for use in the invention can be any suitably activated material known in the art. The material normally has a surface area of at least 1 $m^2/g$. The magnesia can be naturally occurring, such as the mineral Brucite, or can be synthetically prepared by suitable techniques. Minor amounts of other materials such as silica, alumina, and the like, can be present, but the preferred material is principally magnesium oxide. Depending upon the contacting technique used for the olefin conversion reaction, the activated magnesium can be in the form of pellets, extrudates, agglomerates, or even a fine powder. Before use in the process, the magnesium oxide is activated in a suitable manner such as for example by heating in a flowing stream of an oxygen-containing gas for about 1 to 30 hours at about 250° to about 800° C.; preferably for good results in a reasonably short period of time, 300° to about 600° C. After calcination, the magnesium oxide is optionally treated under reducing conditions analogous to those treatment conditions described above with respect to the first catalyst component. Thus, magnesium oxide is treated with a reducing gas such as for example carbon monoxide, hydrogen or a hydrocarbon at a temperature in the range of about 400°–750° C. to enhance the activity of the magnesium oxide. Such reducing treatment is carried out preferably at about 500°–650° C., because good catalyst activation with reasonably short activation periods of about one to about six hours is achieved. Such optional reducing treatment can suitably be carried out for a period of time ranging from about 1 minute to about 30 hours. After activation sometimes it is advisable to flush the catalyst with an inert gas to remove any adsorbed oxygen or other gases from the magnesium oxide. The regeneration of magnesium oxide catalyst is generally accomplished by a technique which is similar to the activation of this material and can be carried out simultaneously with the regeneration and activation of the first catalyst component with which it is being utilized.

When preparing a mixed bed of the first catalyst component and the second catalyst component, particles of the first catalyst component and particles of the second catalyst component of about the same particle size can be blended. Alternatively, both the first catalyst component and the second catalyst can be intimately blended such as by grinding and the powder then formed into other shapes such as pellets, tablets, agglomerates, extrudates, and the like, such that each particle in the catalytic zone comprises an intimate blend of the two catalyst components.

Other appropriate techniques for obtaining a composite of the two catalyst components can be used.

The proportion of second catalyst component to the first catalyst component in the composite catalyst system can vary widely. At least about 0.1 part by weight of the second catalyst component should be present for each part by weight of the first catalyst component. There is no theoretical upper limit for the amount of the second catalyst component which can be present. Preferred ratios, for ease of catalyst blending, are about 0.5 to about 20 parts by weight of the second catalyst component per part by weight of the first catalyst component. Ratios of about 2 to about 10 parts by weight of the second catalyst component per part by weight of the first catalyst component are especially preferred because excellent catalyst performance is obtained.

Catalysts according to the invention are useful, for example, for the conversion of olefins via the olefin disproportionation or olefin metathesis reaction.

Reactants

The process of the present invention comprises contacting at least one olefin selected from the group consisting of acyclic mono- and polyenes having at least three carbon atoms per molecule and cycloalkyl and aryl derivatives thereof; cyclic mono- and polyenes having at least four carbon atoms per molecule and alkyl and aryl derivatives thereof; mixtures of two or more of the above olefins; and mixtures of ethylene with one or more of the above olefins capable of undergoing disproportionation with catalysts prepared according to the invention. Although not limited thereto, olefins employed in the practice of the invention will preferably have up to about 30 carbon atoms, since longer chain olefins are more difficult to handle than olefins of about 30 carbon atoms or less. Where mixtures of the above olefins with ethylene are subjected to disproportionation reaction conditions, it is desirable that the molar ratio of ethylene to olefin be at least 2. Preferably, ethylene:olefin ratios of about 4:1 or higher will be employed for good results.

Some specific examples of olefins suitable for reactions of this invention include propylene, 1-butene, 2-butene, 1-pentene, 2-pentene, 2,4,4-trimethyl-2-pentene and 2,4,4-trimethyl-1-pentene(diisobutylene isomers), 1-hexene, 1,4-hexadiene, 2-heptene, 1-octene, 2,5-octadiene, 2-nonene, 1-dodecene, 2-tetradecene, 1-hexadecene, 1-phenyl-2-butene, 4-octene, 3-eicosene, 3-hexene, vinylcyclohexane, 1,4-pentadiene, 1,4,7-dodecatriene, 2-methyl-4-octene, 4-vinylcyclohexene, 1,7-octadiene, 1,5,9,13,17-octadecapentaene, 8-cyclopentyl-4,5-dimethyl-1-decene, 6,6-dimethyl-1,4-octadiene, and 3-heptene, and the like, and mixtures of two or more thereof.

Some specific examples of cyclic olefins suitable for the reactions of this invention are cyclobutene, cyclopentene, cycloheptene, cyclooctene, 5-n-propylcyclooctene, cyclodecene, cyclododecene, 3,3,5,5-tetramethylcyclononene, 3,4,5,6,7-pentaethylcyclodecene, 1,5-cyclooctadiene, 1,5,9-cyclodecatriene, 1,4,7,10-cyclododecatetraene, 6-methyl-6-ethyl-1,4-cyclooctadiene and the like, and mixtures of two or more thereof.

DISPROPORTIONATION REACTION CONDITIONS

A combined catalyst comprising a first catalyst component comprising a silica support with an oxide of tungsten or a precursor of an oxide of tungsten and a Group I oxide or compound convertible to the oxide admixed with a second catalyst component as hereinbefore described is useful, for example, for the conversion of olefins via the olefin disproportionation reaction.

The reaction temperature can vary depending upon the catalyst and feed(s) employed and upon the desired reaction products. Typically the disproportionation is carried out at a temperature in the range of about 0° to about 600° C.; preferably for good conversion in relatively short reaction times, temperatures of from about 20° to about 500° C. are employed.

The disproportionation reaction can be carried out by contacting the olefins to be disproportionated with the combined catalyst in the liquid phase or the gas phase depending on structure and molecular weight of the olefin. Pressure during the disproportionation reaction can vary between wide limits. For example, pressures between 0.1 and 500 atmospheres are suitable, although preferred pressures are between about 1 and 40 atmospheres because good conversions are obtained with readily available equipment.

If the reaction is carried out in the liquid phase, solvents or diluents for the reactants can be used. Aliphatic saturated hydrocarbons e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, e.g. nitrogen, argon, can be present. Preferably, for high product yield, the disproportionation reaction is effected in the absence of significant amounts of deactivating materials such as water and oxygen.

The contact time needed to obtain a reasonable yield of disproportionation products depends upon several factors such as the activity of the combined catalyst, temperature, pressure and structure of the olefinically unsaturated compound(s) to be disproportionated. Length of time during which the olefinic unsaturated compounds to be disproportionated are contacted with the catalyst can conveniently vary between 0.1 seconds and 24 hours although longer and shorter contact times can be used. Preferably, for efficient use of reactor equipment, times of about 1 second to about 1 hour are used.

The process of the invention can be effected batchwise or continuously with fixed catalyst beds, slurried catalyst, fluidized beds, or by using any other conventional contacting techniques.

Products

The olefinic products of the invention have established utility including use as precursors of polymers, e.g., as the third component of ethylene-propylene terpolymers useful as synthetic elastomers. Cleavage of the ethylenic bonds of polyolefinic products as by ozonization produces di- or polycarboxylic acids which are reacted with diamines, e.g., hexamethylenediamine, to form polyamides which are useful in synthetic fibers. The olefinic products are converted to secondary and tertiary alcohols as by sulfuric acid-catalyzed hydration. Alternatively, the olefinic products are converted by conventional "Oxo" processes to aldehydes which are hydrogenated with conventional catalysts to the corresponding alcohols. The $C_{12}$–$C_{20}$ alcohols thereby produced are ethoxylated as by reaction with ethylene oxide in the presence of a basic catalyst, e.g., sodium hydroxide, to form conventional detergents and the lower molecular weight alcohols are esterified by reaction with polybasic acids, e.g., phthalic acid, to form plasticizers for polyvinyl chloride.

A further understanding of the present invention and its advantages will be provided by reference to the following examples.

EXAMPLE I (Catalyst Preparation)

Catalyst component A which contained 7.2 wt. % $WO_3$ on silica was prepared by impregnating low sodium, low aluminum, high surface area silica (Davison G57 silica, 300 m²/g; 0.1 wt. % $Na_2O$; 0.05 wt. % $Al_2O_3$) with 0.08 grams of ammonium metatungstate ($(NH_4)_2W_4O_{13}.8H_2O$) per gram of silica. The impregnation was accomplished by treating the silica with an aqueous solution of ammonium metatungstate. The impregnated silica was over dried and calcined in air at 538° C. for 8 hours. A $-20+40$ mesh sieve fraction was obtained for use.

Catalyst component B was prepared in similar fashion to catalyst A, except 0.002 g of potassium hydroxide per gram of silica was added to the ammonium metatungstate-containing treating solution. The final catalyst contained 7.2 wt. % $WO_3$ and about 0.2 wt. % $K_2O$.

Catalyst component C was prepared in similar fashion to catalyst component B, except only 0.001 g. of potassium hydroxide per gram of silica was employed. The final catalyst thus contained 7.2 wt. % $WO_3$ and about 0.1 wt. % $K_2O$.

Catalyst component D was a commercially prepared silica supported catalyst (Davison Chemical Co., SMR-9-1413; 246 m²/g; 0.08 wt. % $Na_2O$; 0.09 wt. % $Al_2O_3$) with 7.0 wt. % $WO_3$.

Catalyst component E was prepared by impregnating catalyst component D with an aqueous solution of potassium hydroxide to give a final catalyst, after calcination, containing about 0.1 wt. % $K_2O$.

EXAMPLE II

Disproportionation of Ethylene plus Diisobutylene

All runs were made by passing ethylene and a mixture of diisobutylene isomers (2,4,4-trimethyl-1-pentene and 2,4,4-trimethyl-2-pentene) downflow through a vertical pipe reactor (½ inch diameter and 20 inches in length) positioned in a temperature-controlled electric furnace. A thermocouple was positioned in the catalyst bed to monitor reaction temperature.

About 5 inches depth of alpha-alumina particles were placed at the bottom of the pipe reactor supported with a layer of glass wool. The bed of alpha-alumina particles supported an admixture of 4.3 grams (g) $WO_3/SiO_2$ and 10.7 g activated (at 538° C.) MgO. This was topped with another layer of glass wool and the remaining reactor space filled with alpha-alumina. The catalyst was activated by heating at 538° C. in flowing air for 8 hrs followed by a 30 minute treatment with flowing carbon monoxide at 538° C.

Ethylene used in the reaction was passed through a 13X mol sieve drier and diisobutylene employed was passed over a magnesium oxide guard bed. Feed was introduced into the reactor maintained at about 373° C. and 400 psig pressure. An ethylene:diisobutylene molar ratio of about 2:1 was introduced at a diisobutylene feed rate of about 3 weight hourly space velocity (WHSV). Product samples were collected in a high pressure syringe and were analyzed in a Hewlett Packard Model 5840 gas chromatograph using a ⅛"×20' column packed with 10% OV101 (dimethylsilicone available from Supelco, Inc., Bellefonte, Pa.) on Chromosorb P (red diatomaceous earth available from Applied Science, Deerfield, Ill.). Reaction results are summarized in Table I. Conversion of diisobutylene (Conv) and selectivity to neohexane (Sel) values presented in Table I are calculated as weight % of total reactor effluent.

TABLE I

| Reaction time, hrs. | Run No. (Catalyst Composition) | | | |
|---|---|---|---|---|
| | Run 1 (A + MgO; control) | | Run 2 (B + MgO; invention) | |
| | Conv | Sel | Conv | Sel |
| 3/4 | 78.9 | 48.1 | 79.7 | 85.5 |
| 1 3/4 | 81.8 | 61.4 | 83.6 | 89.4 |
| 2 3/4 | 78.3 | 60.4 | 80.6 | 90.9 |
| 3 3/4 | 75.8 | 48.2 | 78.4 | 86.8 |
| 4 3/4 | 72.8 | 38.6 | 72.0 | 89.9 |

The data in Table I show that the catalyst composition of the invention (Run 2) shows generally improved conversion and dramatically improved selectivity compared to a prior art catalyst composition (Run 1).

EXAMPLE III

Disproportionation of Ethylene plus 2-Butene

All runs were made by passing ethylene and a mixture of cis- and trans-2-butene downflow through a vertical pipe reactor (½ inch diameter and 20 inches in length) positioned in a temperature-controlled electric furnace. A thermocouple was positioned in the catalyst bed to monitor reaction temperature.

About 6 inches depth of quartz chips (−9+12 mesh) were placed at the bottom of the pipe reactor supported by a layer of quartz wool. Another layer of quartz wool was placed on top of the quartz chips as support for a combined catalyst bed comprising about 1.5 g of silica supported $WO_3$ catalyst mixed with about 4.5 g of a second catalyst component as indicated in Table II. This was topped with another layer of quartz wool and the remainder of the reactor filled with quartz chips. The combined catalyst was activated by heating at 538° C. in flowing air for three hours, followed by about 15-minute treatment with flowing carbon monoxide at the same temperature and finally the catalyst was cooled under flowing nitrogen to reaction temperature.

Ethylene used in the reaction was passed through a 13X mol sieve drier and butene feedstock was percolated through 13X mol sieve, then alumina and finally magnesium oxide prior to use. Feed introduced into the reactor was maintained at about 400 psig pressure and about 350° C. Ethylene:butene molar ratios of about 10/1 were investigated with 2-butene feed introduced at the rate of about 7.5 weight hourly space volocity (WHSV).

The hot reactor effluent was vented to a hood; periodically the total effluent was sampled using a modified, heated Series A-2 Sample-Lok syringe (Dynatech Precision Sampling Corporation). Analyses were carried out on a ⅛"×20' OV-101 column at an initial temperature of 50° C. programmed up to 200° C. Reaction results are summarized in Table II. Conversion of 2-butene (Conv) and selectivity to propylene (Sel) values presented in Table II are calculated as weight percent.

TABLE II

| Reaction time, hrs. | Run No. (Catalyst Composition) | | | |
|---|---|---|---|---|
| | Run 3 (D + MgO; control) | | Run 4 (E + MgO; invention) | |
| | Conv | Sel | Conv | Sel |
| 1 | 85.3 | 95.8 | 94.2 | 99.1 |
| 1½ | 85.4 | 96.5 | — NS* | — |
| 2 | 84.5 | 96.6 | 94.3 | 99.1 |
| | Run 5 (C + α-Al₂O₃; control) | | Run 6 (C + MgO; invention) | |
| | Conv | Sel | Conv | Sel |
| ½ | 40.7 | 98.6 | 94.5 | 98.2 |
| 1 | — NS* | — | 94.0 | 99+ |
| 1½ | 48.0 | 97.9 | 94.2 | 99.2 |

*Not Sampled

Comparison of Run 3 and Run 4 demonstrates that higher conversion and selectivity result with the invention catalyst composition. Similarly, comparison of Run 5 employing catalyst component C admixed with a second catalyst component known to be active for skeletal isomerization (rather than double bond isomerization), i.e., $\alpha$-$Al_2O_3$, gave much lower feed conversion than did Run 6 employing the inventive composition comprising an admixture of catalyst component C with MgO.

That which is claimed:

1. A process comprising contacting at least one olefin selected from the group consisting of acyclic mono- and polyenes having at least 3 carbon atoms per molecule and cycloalkyl and aryl derivatives thereof; cyclic mono- and polyenes having at least 4 carbon atoms per molecule and alkyl and aryl derivatives thereof; mixtures of two or more of the above olefins; and mixtures of ethylene with one or more of the above olefins capable of undergoing disproportionation with a combined catalyst consisting essentially of:
    (a) a first catalyst component consisting essentially of:
        (i) a silica support,
        (ii) an oxide of tungsten or a precursor of an oxide of tungsten, and
        (iii) a Group I oxide or compound convertible to the oxide; and
    (b) a second catalyst component consisting essentially of a double bond isomerization catalyst in admixture with said first catalyst component.

2. A process according to claim 1 wherein said combined catalyst is treated in the presence of an oxygen-containing gas at about 350° C. to about 800° C. for about 15 minutes to about 20 hours prior to contacting said at least one olefin with said combined catalyst.

3. A process according to claim 3 wherein said combined catalyst is further treated under reducing conditions at about 400°–750° C. for about 1 minute to about 30 hours prior to contacting said at least one olefin with said combined catalyst.

4. A process according to claim 1 wherein said oxide of tungsten is $WO_3$.

5. A process according to claim 1 wherein said oxide of tungsten or precursor of an oxide of tungsten is present in an amount of at least about 0.1 wt. % of the metal, calculated as the oxide, and based on the combined weight of the tungsten oxide and silica support.

6. A process according to claim 1 wherein said Group I oxide or compound convertible to the oxide is a compound of sodium or potassium selected from the group consisting of:
    oxides,
    hydroxides, carbonates,
bicarbonates,
nitrates,
acetates,
and mixtures of any two or more thereof.

7. A process according to claim 1 wherein said Group I oxide or compound convertible to the oxide is present in an amount from about 0.01 to about 10 wt. % of the metal, calculated as the oxide and based on the combined weight of the Group I oxide and silica supports.

8. A process according to claim 1 wherein said second catalyst component is selected from the group consisting of:
magnesium oxide,
calcium oxide,
cerium oxide,
thorium oxide,
titanium oxide,
zinc oxide,
and mixtures of any two or more thereof.

9. A process according to claim 3 wherein said at least one olefin comprises a mixture of ethylene and cis-2-butene and trans-2-butene.

10. A process according to claim 3 wherein said at least one olefin comprises a mixture of ethylene and a mixture of diisobutylene isomers (2,4,4-trimethyl-1-pentene and 2,4,4,-trimethyl-2-pentene).

11. A process comprising contacting at least one olefin selected from the group consisting of acyclic mono- and polyenes having at least 3 carbon atoms per molecule and cycloalkyl and aryl derivatives thereof; cyclic mono- and polyenes having at least 4 carbon atoms per molecule and alkyl and aryl derivatives thereof; mixtures of two or more of the above olefins; and mixtures of ethylene with one or more of the above olefins capable of undergoing disproportionation with a combined catalyst consisting essentially of:

(a) a first catalyst component consisting essentially of:
  (i) a silica support with a surface area of at least about 10 m$^2$/g, about 0.2 wt. % or less aluminum, measured as $Al_2O_3$ and about 0.2 wt. % or less sodium, measured as $Na_2O$,
  (ii) at least about 0.1 wt. % of tungsten oxide ($WO_3$) based on the combined weight of tungsten oxide and silica support, and
  (iii) about 0.01 to about 10 wt. % of potassium hydroxide calculated as the oxide and based on the combined weight of potassium oxide and silica support; and (b) a second catalyst component consisting essentially of magnesium oxide; wherein said first catalyst component and said second catalyst component are admixed in a weight ratio of about 1:0.5 to about 1:20.

* * * * *

UNITED STATES PATENT AND TRADEMARK OFFICE
CERTIFICATE OF CORRECTION

PATENT NO. : 4,575,575
DATED : March 11, 1986
INVENTOR(S) : Charles A. Drake, Robert E. Reusser It is certified that error appears in the above-identified patent and that said Letters Patent is hereby corrected as shown below:

Claim 3, line 1, "3" should be ---2---.

Signed and Sealed this

Twenty-fourth Day of June 1986

[SEAL]

Attest:

DONALD J. QUIGG

Attesting Officer

Commissioner of Patents and Trademarks

Disclaimer 4,575,575.—*Charles A. Drake; Robert E. Reusser*, both of Bartlesville, Okla. CATALYSTS AND PROCESS FOR OLEFIN CONVERSION. Patent dated Mar. 11, 1986. Disclaimer filed Jan. 30, 1989, by the assignee, *Phillips Petroleum Co.*

Hereby enters this disclaimer to all claims of said patent.
[*Official Gazette April 18, 1989.*]

Disclaimer 4,575,575.—*Charles A. Drake and Robert E. Reusser*, both of Bartlesville, Okla. CATALYSTS AND PROCESS FOR OLEFIN CONVERSION. Patent dated Mar. 11, 1986. Disclaimer filed Jan. 30, 1989, by the assignee, Phillips Petroleum Co.

Hereby enters this disclaimer to all claims of said patent.
[*Official Gazette May 2, 1989*.]